United States Patent
Ghazizadeh et al.

(10) Patent No.: US 7,632,431 B2
(45) Date of Patent: Dec. 15, 2009

(54) COMPOSITE INTRAOCULAR LENS AND METHOD OF MANUFACTURE THEREOF

(75) Inventors: Massoud Ghazizadeh, Laguna Hills, CA (US); Harish Makker, Mission Viejo, CA (US)

(73) Assignee: Abbott Medical Optics Inc., Santa Ana, CA (US)

( * ) Notice: Subject to any disclaimer, the term of this patent is extended or adjusted under 35 U.S.C. 154(b) by 413 days.

(21) Appl. No.: 11/317,154

(22) Filed: Dec. 22, 2005

(65) Prior Publication Data

US 2006/0097413 A1    May 11, 2006

(51) Int. Cl.
*B29D 11/00*    (2006.01)
(52) U.S. Cl. .................................. 264/1.7; 264/2.7
(58) Field of Classification Search .............. 264/1.1, 264/1.7, 2.7; 425/808
See application file for complete search history.

(56) References Cited

U.S. PATENT DOCUMENTS

| | | | |
|---|---|---|---|
| 4,093,361 A | 6/1978 | Erickson et al. | |
| 4,409,691 A | 10/1983 | Levy | |
| 4,571,039 A | 2/1986 | Poler | |
| 4,687,485 A | 8/1987 | Lim et al. | |
| 4,718,906 A | 1/1988 | Mackool | |
| 4,764,169 A | 8/1988 | Grendahl | |
| 4,990,159 A | 2/1991 | Kraff | |
| 4,997,442 A | 3/1991 | Barrett | |
| 5,217,491 A | 6/1993 | Vanderbilt | |
| 5,236,970 A | 8/1993 | Christ et al. | |
| 5,306,297 A | 4/1994 | Rheinish et al. | |
| 5,376,694 A | 12/1994 | Christ et al. | |
| 5,494,946 A | 2/1996 | Christ et al. | |
| 5,496,366 A | 3/1996 | Cumming | |
| 5,549,668 A | 8/1996 | O'Donnell, Jr. | |
| 5,661,195 A | 8/1997 | Christ et al. | |
| 5,674,282 A | 10/1997 | Cumming | |
| 5,869,549 A | 2/1999 | Christ et al. | |
| RE36,150 E | 3/1999 | Gupta | |
| 6,015,511 A * | 1/2000 | Yasuda et al. | 264/1.7 |
| 6,176,878 B1 | 1/2001 | Gwon et al. | |
| 6,231,603 B1 | 5/2001 | Lang et al. | |
| 6,406,494 B1 | 6/2002 | Laguette et al. | |
| 6,425,917 B1 | 7/2002 | Blake | |
| 2002/0120330 A1 | 8/2002 | Galin | |
| 2003/0187505 A1* | 10/2003 | Liao | 623/6.37 |

FOREIGN PATENT DOCUMENTS

JP        198126 A    1/1999

* cited by examiner

*Primary Examiner*—Mathieu D. Vargot

(57) ABSTRACT

An intraocular lens includes an optic adapted to focus light toward a retina of an eye, and at least one fixation member configured to at least assist in supporting the optic in the eye. The fixation member includes a proximal portion coupled to the optic and a distal portion configured to be in contact with eye tissue when the intraocular lens is in use in the eye. The proximal portion of the fixation member includes at least one first area formed of a first, substantially rigid material, and at least one second area formed of a second material which is more flexible than the first material.

18 Claims, 2 Drawing Sheets

COMPOSITE INTRAOCULAR LENS AND METHOD OF MANUFACTURE THEREOF

The present application claims priority under 35 U.S.C. §120 of U.S. application Ser. No. 10/355,586 filed Jan. 30, 2003, which is incorporated by reference herein in its entirety.

BACKGROUND OF THE INVENTION

This invention relates to intraocular lenses (IOLs). More particularly, the invention relates to deformable, e.g., foldable, IOLs for placement in eyes, e.g., in the anterior chambers of eyes, and to methods of making and using such IOLs.

The human eye is susceptible to numerous disorders and diseases, a number of which attack the crystalline lens. For example, cataracts mar vision through cloudy or opaque discoloration of the lens of the eye, and can result in partial or complete blindness. When this happens, the crystalline lens can be removed and replaced with an intraocular lens, or IOL. In certain other circumstances, an IOL can be placed in an eye containing the natural crystalline lens, for example, to provide for enhanced vision in the phakic eye. A typical IOL comprises an optic body, or lens, adapted to focus light toward the retina of the eye, and one or more fixation members, or haptics, adapted to at least assist in supporting or fixating the IOL in a suitable location in the eye, such as the anterior chamber, iris, or capsular bag of the eye.

The optic and haptics may be formed as an integral unit from a single material, but in recent years the trend has been toward composite IOLs which use different materials for the various components, so that the properties of these components can be separately optimized. Examples of such composite IOLs are shown in Barrett U.S. Pat. No. 4,997,442 and Vanderbilt U.S. Pat. No. 5,217,491, both of which employ relatively flexible materials in the optic portion and more rigid materials in the haptics. The disclosure of each of these patents is incorporated in its entirety herein by reference. In both the Barrett composite IOL and the Vanderbilt composite IOL, the flexible material of the optic enables the IOL to be deformed, e.g., folded, rolled and the like, for insertion through a small surgical incision in the eye, while the relatively rigid material of the haptics enhances the stability of the optic in the eye.

In most, if not all, prior art composite IOLs, such as those disclosed by Vanderbilt and Barrett, the haptics have been configured as extremely thin, filament or loop-type members suitable for securing the optic in the posterior chamber, or capsular bag, of the eye. The slenderness of these types of fixation members to some degree compensates for the rigidity of the material from which they are made, and enables such fixation members to be curled, folded, or wound up inside a conventional inserter cartridge, without significantly interfering with the folding of the optic. However, such filament or loop type fixation members are generally not recommended for use in the anterior chamber of the eye.

More particularly, anterior chamber IOLs are subject to different conditions than posterior chamber IOLs, and thus differ significantly in their design. For instance, anterior chamber IOLs must be able to withstand the relatively high compressive forces exerted by the surrounding structure of the anterior chamber without allowing significant movement of the optic. In addition, anterior chamber IOLs should be structured to reduce the potential for complications such as pupil ovalling, endothelial cell loss and the like.

Various designs for anterior chamber IOLs are disclosed in Nigam U.S. Pat. No. 5,982,282. Other designs are disclosed in Laguette et al. co-pending U.S. patent application Ser. No. 09/908,515, Nguyen et al. co-pending U.S. patent application Ser. No. 09/847,957, Laguette co-pending U.S. patent application Ser. No. 09/847,958 and Paul co-pending patent application Ser. No. 10/225,990. Each of these co-pending applications and the present application are commonly owned. The disclosure of each of the Nigam patent and the above co-pending U.S. patent applications is hereby incorporated in its entirety by reference herein.

Although the anterior chamber IOLs disclosed in the above patent applications perform satisfactorily in most respects, they all include relatively large fixation members which, if made entirely of rigid material such as poly methylmethacrylate (PMMA), might interfere with the ability of the IOLs to be deformed for insertion into eyes through small incisions. It is advantageous to insert in an IOL though such a small incision to obtain benefits, for example, reduced surgical trauma, reduced recovery time and the like.

Accordingly, it would be advantageous to provide foldable IOLs, for example, anterior chamber IOLs, with fixation members having sufficient rigidity to maintain optic stability in the eye, while still being flexible or deformable enough to allow the IOL to be folded or otherwise deformed for insertion through a small, or even a very small, incision in the eye. In addition, it would be advantageous to provide such IOLs with configurations that are compatible for use with conventional insertion apparatus. It would also be advantageous to devise methods of manufacturing such IOLs that are relatively simple and cost-effective.

SUMMARY OF THE INVENTION

New IOLs for implantation in eyes, for example in anterior chambers of the eyes, as well as methods of making and using such IOLs have been discovered. The present IOLs are sized and structured to reduce the incidence of one or more known complications in the eye caused by prior IOLs, and to be foldable for effective and safe insertion through small or very small incisions in the eye using, for example, conventional insertion apparatus.

In accordance with one aspect of the present invention, an intraocular lens comprises an optic adapted to focus light toward a retina of an eye, and at least one fixation member configured to secure the optic in the eye. The fixation member includes a proximal portion coupled to the optic and a distal contact portion configured to be in contact with eye tissue when the intraocular lens is in use in the eye. The proximal portion of the fixation member includes at least one first area formed of a first, substantially rigid material, and at least one second area formed of a second material which is less rigid or more flexible than the first material.

In one embodiment, the fixation member is configured to secure the optic in an anterior chamber of an eye. The proximal portion of the fixation member includes at least two segments formed of the first, substantially rigid, material, preferably extending generally in a first direction and a different second direction, respectively, relative to the optic. In one useful version of this embodiment, the first segment extends generally radially with respect to the optic, and the second segment extends generally circumferentially with respect to the optic. An area between the two segments is formed of the second, more flexible material.

In a particularly useful embodiment, the optic is formed of a deformable, e.g., resiliently deformable, or foldable material, preferably a material allowing the optic to be folded or rolled for insertion through an incision measuring about 3.5 mm or less. Preferably this material is the same as the second material. In one version of this embodiment, the first and second materials are acrylic-based polymeric materials. For instance, the first material may be poly methylmethacrylate (PMMA), and the second material may be an acrylic-based polymeric material compatible with PMMA.

A method of producing an IOL according to the present invention comprises a step of forming a composite member into an intraocular lens having an optic adapted to focus light toward the retina of an eye and at least one fixation member configured to secure the optic in the eye, wherein the fixation member includes a proximal portion coupled to the optic, and a distal contact portion configured to be in contact with eye tissue when the intraocular lens is in use in the eye, and wherein the proximal portion includes at least one first area formed of a first, substantially rigid material and at least one second area formed of a second material less rigid or more flexible than the first material.

In one useful embodiment, the method further comprises a step of producing the composite member, preferably by polymerizing a first monomeric component to obtain the first material, and polymerizing a second monomeric component to obtain the second material.

In an especially useful embodiment, the step of polymerizing a first monomeric component comprises polymerizing a first acrylic-based polymeric precursor material within a mold, and the step of polymerizing a second monomeric component comprises polymerizing a second acrylic-based polymeric precursor material, compatible with the first material, within a cavity formed in the polymerized first material.

A method of correcting vision according to the present invention comprises providing an intraocular lens in a compressed configuration. The intraocular lens includes an optic adapted to focus light toward a retina of an eye, and at least one fixation member configured to at least assist in supporting the optic in an eye. The fixation member includes a proximal portion coupled to the optic and a distal portion configured to be in contact with eye tissue when the intraocular lens is in use in the eye. The proximal portion includes at least one first area formed of a first, substantially rigid material and a second area formed of a second material less rigid or more flexible than the first material. The compressed intraocular lens is inserted through a small incision in the eye, and preferably positioned within the anterior chamber, for use.

Each and every feature described herein, and each and every combination of two or more of such features, is included within the scope of the present invention provided that the features included in such a combination are not mutually inconsistent.

Additional aspects and advantages of the present invention are set forth in the following description and claims, particularly when considered in conjunction with the accompanying drawings in which like parts bear like reference numerals.

DESCRIPTION OF THE PREFERRED EMBODIMENTS

Figure 1:
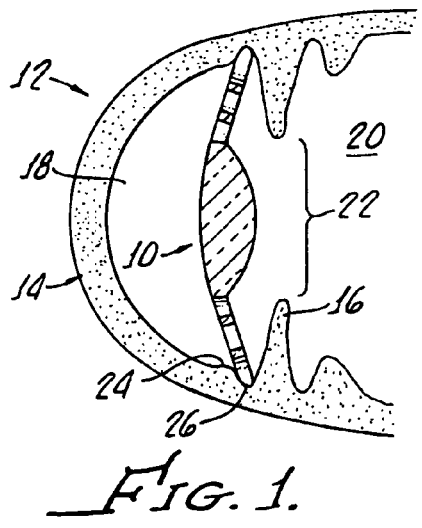
FIG. 1 is a vertical sectional view of an eye and an exemplary anterior intraocular lens of the present invention implanted therein.

Referring now to FIG. 1, an anterior chamber IOL 10 according to the present invention is shown implanted in an eye. For ease of illustration, the illustrated eye is aphakic; that is, the natural crystalline lens has been removed. It will be apparent to one of ordinary skill in the art, however, that an anterior chamber IOL 10 according to the present invention may also, and often will, be used in an eye having the natural crystalline lens in place—in other words, a phakic eye.

The eye 12 comprises a cornea shown to the left and an iris 16 shown in the middle of the eye. It is to be understood that the cornea 14 is at the front of the eye 12. The iris 16 divides the eye into an anterior chamber 18 at the front of the eye and a posterior chamber 20 in front of the iris 16. The iris 16 also defines the pupil 22, which is an opening in the middle of the iris 16. In front of the iris 16 is the scleral spur 24. The scleral spur and the iris 18 delimit the ciliary band 26.

Figure 2:
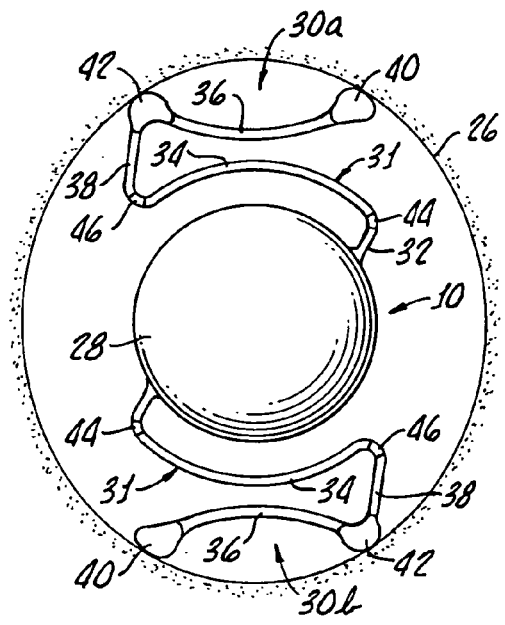
FIG. 2 is a top plan view of an intraocular lens according to the present invention.

The IOL 10, shown in greater detail in FIG. 2, includes a central optic 28 and a pair of fixation members 30a, b. The illustrated number and structure of the fixation members is merely exemplary, as the principles of the present invention may be applied to a large variety of anterior chamber IOLs including, but not limited to, the IOLs disclosed in Laguette et al. co-pending U.S. patent application Ser. No. 09/908,515, Nguyen et al. co-pending U.S. patent application Ser. No. 09/847,957, Laguette co-pending U.S. patent application Ser. No. 09/847,958 and Paul co-pending patent application Ser. No. 10/225,990, the contents of all of which are incorporated by reference herein.

As illustrated, each fixation member 30a, b is sinuous in structure, and includes a proximal portion 31 and distal contact portion 40. Each proximal portion 31 has several regions, or segments, including a proximal connector segment 32 that extends radially outwardly from the optic, an elongated intermediate segment 34 that extends generally circumferentially from a distal end of the connector portion 32, and a distal segment or elongated member 36 that is configured to extend generally along a chordal line with respect to the ciliary band 26 when the IOL 10 is positioned in the anterior chamber 18 of eye 12. A bridge segment 38 extends generally perpendicularly between a distal end of the intermediate segment 34 and a proximal end of the distal segment 36. The distal contact portion 40, also called a pod or footplate, is enlarged and somewhat bulbous, to minimize contact stress on, and reduce the potential for trauma to, the ocular tissue in the anterior chamber of the eye.

The optic 28 of the IOL 10 is advantageously made from a sufficiently flexible material to enable the IOL 10 to be resiliently deformed, e.g., folded or rolled, for insertion through a small incision, for example an incision of about 3.5 mm long or less, such as about 3.2 mm or less, or about 3.0 mm or less, and preferably no more than about 2.8 mm long. One preferred optic material meeting these requirements is the acrylic polymeric material from which the optic of an IOL marketed under the trademark SENSAR® by Advanced Medical Optics, Inc. is made. The optic of the SENSAR® IOL is made of a cross-linked acrylic polymeric material formed of copolymers of methacrylate and acrylate esters, cross-linked with a diacrylate ester to produce the cross-linked acrylic copolymer. Useful deformable cross-linked acrylic polymeric materials are disclosed in Gupta U.S. Reissue Pat. No. RE36,150, the disclosure of which is incorporated in its entirety herein by reference.

The proximal portion 31 of each of the fixation members 30a and b includes at least one area made of a substantially rigid first material, for instance poly methylmethacrylate (PMMA), and at least one area made of a second material which is more flexible than the first material. In the illustrated embodiment, proximal connector segment 32, intermediate segment 34, distal segment 36, and bridge segment 38 are all made of the first material, and regions or areas 44, 46, and 42 are made of the second material. The number and location of flexible areas may vary, depending on the structure of the fixation members 30a, b. In one useful embodiment, the flexible areas are located at areas of the fixation members subject to increased stress, for example, areas where the possibility of breakage would be increased or even highest if the fixation members were made entirely of the first material. In sinuous fixation members, such high stress areas often exist at each bend or substantially sharp change in direction along the length of the fixation member. In the illustrated embodiment, there are three such bends in each fixation member 30a, b: a first bend at the intersection between proximal portion 32 and intermediate portion 34; a second bend at the intersection between intermediate portion 34 and bridge portion 38; and a third bend at the intersection between bridge portion 38 and distal segment 36. Thus, flexible areas 44, 46, and 42 are advantageously located at the first, second and third bends, respectively. These flexible areas 44, 46, and 42, which also may be thought of as joints or elbows, allow the fixation members 30a and b to be resiliently deformed, i.e. folded, thus greatly facilitating the insertion of the IOL 10 through a small incision.

In addition to being less rigid or more flexible than the first material, the second material advantageously is resilient so that the fixation members 30a and b return quickly to substantially their original, uncompressed configurations after insertion into the eye. Advantageously, the second material is the same as the material used in the optic. It is also preferred that the second material is compatible with the first material, for example, so that the two materials can easily be co-processed and/or used effectively and safely together. For instance, the first material may be poly methylmethacrylate (PMMA), and the second material may be a deformable cross-linked acrylic material similar to the materials described in the aforementioned Gupta patent.

In the illustrated embodiment, the flexible area 42 between bridge portion 38 and distal segment 36 is bulbous and serves as a pod or footplate similar to distal contact portion 40. Thus, in addition to facilitating folding, the flexible material in this area 42 reduces contact stresses on the surrounding ocular tissues.

Distal contact portion 40 is shown in FIG. 2 as being formed of the same material as flexible areas 44, 46 and 42. However, in some IOL designs, it may be preferable to make the contact portions of a more rigid material, for instance the same material as proximal connector segment 32, intermediate segment 34, bridge segment 38, and distal segment 36. Alternatively, the bridge segment 38 may be formed of the same flexible material as one or both of the distal contact portions 40, 42.

Figure 3:
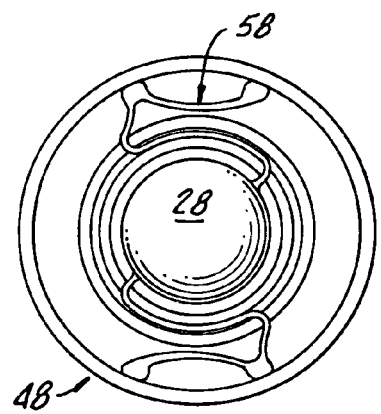
FIG. 3 is a top plan view of a composite button from which the intraocular lens of FIG. 2 may be fabricated.
Figure 4:
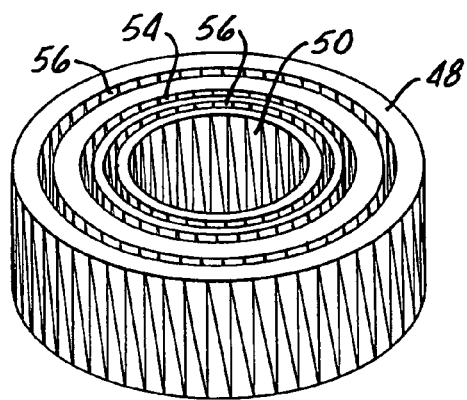
FIG. 4 is a perspective view of a precursor button created during a first step of a method of manufacturing an intraocular lens according to the present invention.
Figure 5:
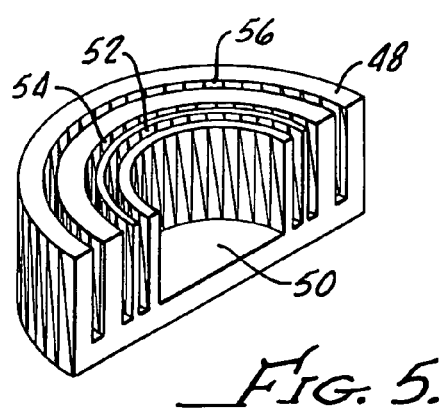
FIG. 5 is a vertical sectional view taken through the precursor button of FIG. 4.

A method of manufacturing IOL 10 will now be described with reference to FIGS. 3-5.

Initially, a first monomeric component, for instance methylmethacrylate precursor material, is poured or otherwise placed in a cylindrical mold (not shown) and polymerized to form a button 48 of substantially rigid material, such as PMMA. A cavity or hole 50 is formed in the central region of the button 48. In the illustrated embodiment, the button 48 has a depth or axial thickness of about 5 mm, and the central cavity has a depth of about 3 to 4 mm. Several smaller, annular cavities or holes 52, 54, 56 are formed radially outwardly of the central cavity 50, at the locations where flexible segments 44, 46 and 42 are desired. These cavities 52, 54, 56 are illustrated herein as being continuous, concentric annular cavities, each having a radial thickness of about 0.5 to 1.0 mm, depending on the desired size of the fixation members and pods. Alternatively, the cavities 52 or 54 could be formed as discrete circular spots or holes (about 0.5 to 1.0 mm in diameter) at the desired locations.

Once the cavities 50, 52, 54, 56 are formed, a second monomeric component, for instance a precursor component of a flexible or deformable cross-linked acrylic polymeric material similar to the materials described in the aforementioned Gupta patent, is polymerized within the cavities 50, 52, 54 and 56 to form flexible rings or spots in the button 48. Finally, the button 48, now having a composite composition, is processed, for example, lathed, cut or otherwise shaped, for instance along the outline 58 shown in FIG. 3, to form the optic 28 and fixation members 30a, b of the IOL 10. In the embodiment shown, the relatively flexible material in the cavities 50, 52, 54, 56 is shaped to form the optic 28, the joints 44, 46 and the contact portions 42, 40, while the stiffer or substantially rigid material of the remainder of the button 48 is shaped to form the proximal connector segments 32, elongated intermediate segments 34, distal segments 36 and bridge segments 38 of the fixation members.

Figure 6:
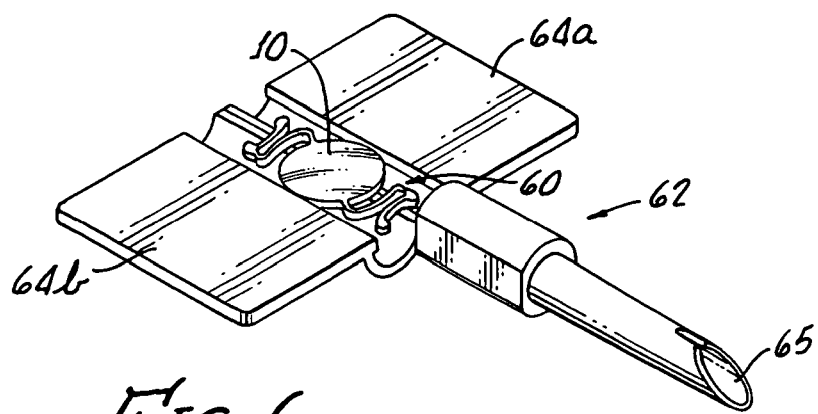
FIG. 6 is a front side view, in perspective, showing an IOL according to the present invention positioned in an open loading cartridge of an insertion apparatus.
Figure 7:
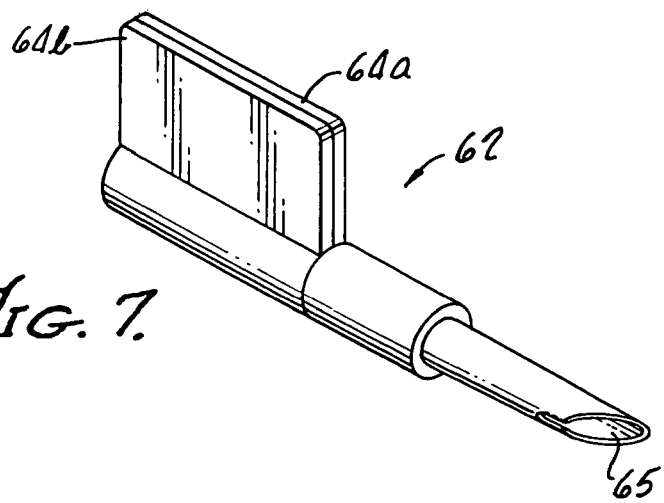
FIG. 7 is a front side view, in perspective, showing the loading cartridge of FIG. 6 is a closed position.
Figure 8:
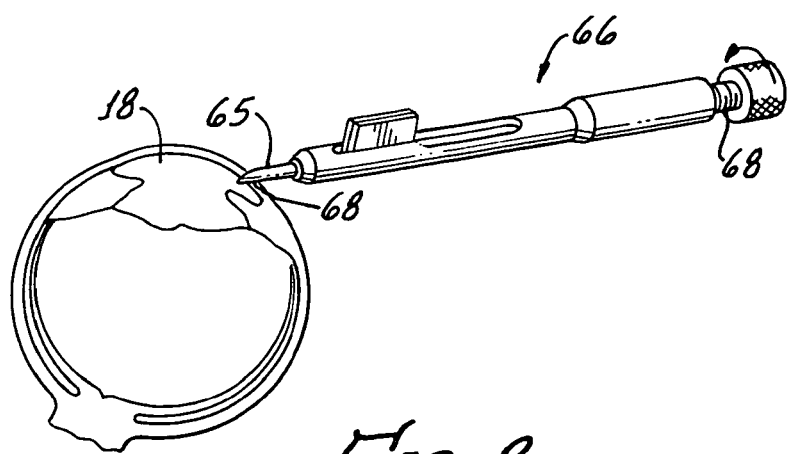
FIG. 8 is a somewhat schematic illustration showing an IOL according to the present invention being inserted in an anterior chamber of an eye.

The IOL 10 can be effectively inserted into an anterior chamber of an eye and used to provide vision correction, for example, vision enhancement. As shown in FIG. 6, an anterior chamber IOL 10 is placed in the load chamber 60 of an IOL insertion cartridge 62 having folding leaves 64a, b and a hollow distal tip 65. The leaves of the cartridge 62 are then moved from their open position, shown in FIG. 6, to their closed position, shown in FIG. 7, bringing both the optic and fixation members into a folded or rolled configuration (not shown). The cartridge 62 is then placed in a suitable insertion apparatus 66 such that the distal tip 65 of the cartridge projects through an distal opening in the insertion apparatus 66. The distal tip 65 of the cartridge is then placed in or near a very small incision 68 in the sclera or cornea of an eye 12, and a plunger 68 or the like is advanced through the insertion apparatus, causing the IOL 10 to be passed through the outlet of the distal tip 65 into the anterior chamber 18 of the eye. Once placed in the anterior chamber 10, the IOL may, if necessary, be repositioned using a needle or the like to obtain optimum stability and centration.

The illustrated insertion apparatus 66 is similar to an apparatus disclosed in Makker U.S. Pat. No. 5,735,858, the disclosure of which is incorporated herein by reference. However, the IOL 10 of the present invention is not limited to use with any particular insertion apparatus, and may in fact be inserted using surgical forceps or other similar devices.

While this invention has been described with respect to various specific examples and embodiments, it is to be understood that the invention is not limited thereto and that it can be variously practiced within the scope of the following claims.

What is claimed:

1. A method of producing an intraocular lens, comprising:
   forming a button from a first material;

forming a central cavity in the button;
forming a discrete additional cavity in the button that is separate from the central cavity; and
disposing a second material within the cavities, the second material being more flexible than the first material;
forming the button and the disposed second material into an intraocular lens having an optic adapted to focus light toward a retina of an eye and at least one fixation member configured to assist in supporting the optic in the eye.

2. The method of claim 1, wherein forming the central cavity comprises forming a circular cavity.

3. The method of claim 1, wherein forming the central cavity or the additional cavity comprises forming a circular cavity or an annular cavity.

4. The method of claim 1, wherein the at least one fixation member includes a first area formed of the first material and a second area formed of the second material.

5. The method of claim 1, wherein the additional cavity is annular.

6. The method of claim 1, wherein the additional cavity is a hole.

7. The method of claim 4, wherein the first area is formed into an elongated segment of the at least one fixation member, the second area is formed into the optic, and the third area is formed into a joint of the at least one fixation member.

8. The method of claim 7, wherein the at least one fixation member includes at least one third area formed of a third material which is more flexible than the first material.

9. The method of claim 1, wherein the additional cavity is disposed radially outwardly of the central cavity and further comprising forming the optic from the second material disposed in the central cavity.

10. The method of claim 4, wherein the first area formed of the first material is disposed between the optic and the second area formed of the more flexible second material.

11. The method of claim 10, wherein the optic is formed of the second material.

12. A method of producing an intraocular lens, comprising:
forming a button of a first material;
forming a plurality of separated cavities in the first material;
forming a composite member by disposing a second material within the cavities that is more flexible than the first material; and
forming an intraocular lens from the composite member, the intraocular lens comprising an optic and a fixation member, the optic comprising the second material, the fixation member including a first area formed of the first material and a second area formed of the second material;
wherein the first area is radially disposed between the optic and the second material.

13. The method of claim 12, wherein forming the composite member comprises polymerizing a first monomeric component to obtain the first material, and polymerizing a second monomeric component to obtain the second material.

14. The method of claim 13, wherein polymerizing the first monomeric component includes polymerizing the first monomeric component in a mold to produce a molded object.

15. The method of claim 14, wherein polymerizing the second monomeric component comprises polymerizing the second monomeric component within the cavities.

16. The method of claim 12, wherein forming the intraocular lens comprises lathing the composite member.

17. The method of claim 12, wherein forming the intraocular lens comprises cutting the composite member.

18. The method of claim 12, wherein forming the intraocular lens comprises shaping the composite member.

* * * * *

UNITED STATES PATENT AND TRADEMARK OFFICE
CERTIFICATE OF CORRECTION

PATENT NO. : 7,632,431 B2  Page 1 of 1
APPLICATION NO. : 11/317154
DATED : December 15, 2009
INVENTOR(S) : Ghazizadeh et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 771 days.

Signed and Sealed this

Second Day of November, 2010

David J. Kappos
*Director of the United States Patent and Trademark Office*